United States Patent [19]

Holtkamp, Sr.

[11] Patent Number: Plant 6,429

[45] Date of Patent: Nov. 29, 1988

[54] AFRICAN VIOLET PLANT NAMED SUSI

[76] Inventor: Reinhold Holtkamp, Sr., Werther Strasse 112, D4294 Isselberg, Fed. Rep. of Germany

[21] Appl. No.: 21,734

[22] Filed: Mar. 4, 1987

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of African violet named Susi, characterized by its single, frilled, mainly white flowers with red-purple centers; strong, upright flower stems that curve toward the center to form a bouquet above the leaves; profuse flowering; vigorous growth habit, flowering 8–9 weeks after potting, and its long-lasting and non-dropping flowers.

1 Drawing Sheet

The present invention comprises a new and distinct cultivar of African violet plant, botanically known as *Saintpaulia ionantha,* and hereinafter referred to by the cultivar name Susi.

Susi was discovered by applicant as a mutation of Colorado, disclosed in U.S. Plant Pat. No. 4,266, from a bed of flowering plants of Colorado in commercial greenhouses in Nashville, Tenn. in August 1984. The new cultivar was immediately recognized due to its distinctly different flower color. Whereas the parent cultivar Colorado has medium dark purple flower color, the flower color of Susi is mainly white with a large center showing of red-purple.

Subsequent asexual reproduction of Susi by me in Nashville, Tenn. has demonstrated that the combination of characteristics as herein disclosed for the new cultivar are firmly fixed and retained through successive generations of asexual reproduction. Propagation has also confirmed that Susi is similar in all essential respects to Colorado except for its distinctly different flower color.

Susi has not been observed under all possible environmental conditions. The phenotype may vary significantly with variations in environment such as temperature, light intensity and day length. The following observations, measurements and values describe the new cultivar as grown in Nashville, Tenn. under greenhouse conditions which closely approximate those generally used in commercial practice.

The following traits have been repeatedly observed and are determined to be basic characteristics of Susi which in combination distinguish this African violet as a new and distinct cultivar:

(1) Strong upright flower stems curving toward the center.

(2) First flash of flowers form a tight bouquet above the leaves.

(3) Long blooming period.

(4) Profuse flowering on long stems.

(5) Each plant carries up to 8 and more upright flower stems, each of which carries 7–9 flowers.

(6) Vigorous grower, compact habit.

(7) Plant saleable 9–10 weeks after potting.

(8) Medium green velvet leaves, slightly hairy.

(9) Long-lasting, non-dropping single flowers.

(10) Seed capsule pushes slightly through.

(11) After maturity the flowers dry off, and remain on the peduncle without being infected by botrytis.

(12) Medium size flowers with frilled edges, white with purplish-red center.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 2:00 p.m. in Nashville, Tenn.

Botanical classification: *Saintpaulia ionantha,* Ramat., cv. Susi.

Parentage: Mutation of Colorado.

Propagation: The new cultivar holds its distinguishing characteristics through successive propagations by leaf cuttings.

Plant: From 7 cm to 10 cm tall when grown in pots, and approximately 23–25 cm in diameter when fully grown.

*Leaves.*—General form: Oval. Diameter: 45–65 mm. Texture: Soft and hairy. Aspect: Velvety, slightly hairy. Veins: Underside well pronounced, light green, shiny. Color (upper side): Green Group 137B. Color (under side): Green Group 138D. Petiole: Strong, upright, light green, hairy.

*Flowers.*—Buds: Ball-shaped 7–9 mm before opening, partly greenish and partly purplish in color. Sepals: Five (5) spear-shaped, 2 small, 3 larger, hairy. Color: Dark brown. Calyx: Shape: Funnel-shaped. Aspect: Spear-shaped, hairy. Peduncle: Character: Strong, upright, wire-like, hairy. Color: Brownish. Individual flowers: Size: 32–38 mm. Shape: Single, violet-shaped, heavily frilled edges. Color (upper side): White with red-purple 74A center, and radiating outwardly from the center, frequently to an area leaving approximately a ¼ inch band of white on the periphery of the flower. Color (under side): White with 74C. Borne: Each flower stem carries 7–9 flowers on strong, upright wire-like peduncles, producing a tight bouquet above the leaves. Flowering habit: Flowers 8–9 weeks after potting.

*Reproductive organs.*—Stamens: 2. Anthers: 2 filaments with four anther cells. Filaments: 4 mm long, purplish yellow in color. Pollen color: Yellow Group 7A. Styles: 4–5 mm, dark purple with a light green base. Roots: Normally developed, white when young, turning slightly brownish when older.

Disease resistance: Good.

General observations: Susi is a mutation out of Colorado having white flowers with red-purple centers and attractive velvet, medium green leaves. Susi is a vigorous and profuse cultivar. Out of the center, 8 and more strong flower stems appear that are slightly bent toward the center, each carrying 7–9, and more single, frilled flowers. The fully developed flower head has a compact habit, forming a nice bouquet. Approximately 8–9 weeks after potting, the plant is saleable. The flowers are long-lasting and non-dropping and the seed capsule pushes slightly through. In general, as the buds open, the outer edge of the white margin is temporarily light greenish.

I claim:

1. A new and distinct cultivar of African violet named Susi, as described and illustrated, and particularly characterized by its single, frilled, mainly white flowers with red-purple centers; strong, upright flower stems that curve toward the center to form a bouquet above the leaves; profuse flowering; vigorous growth habit, flowering 8–9 weeks after potting, and its long-lasting and non-dropping flowers.

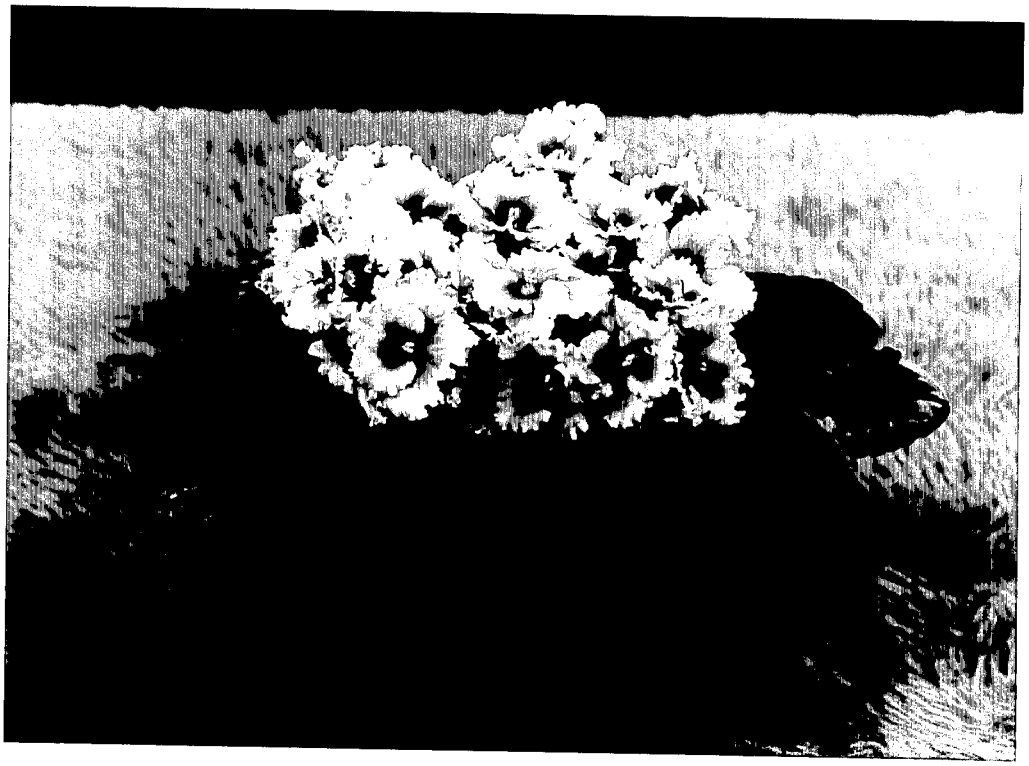

* * * * *